United States Patent [19]
Aucremanne

[11] Patent Number: 5,608,219
[45] Date of Patent: Mar. 4, 1997

[54] DEVICE FOR DETECTING GAS BY INFRARED ABSORPTION

[75] Inventor: Cécile Aucremanne, Maysel, France

[73] Assignee: Saphir, France

[21] Appl. No.: 464,723

[22] Filed: Jun. 27, 1995

[30] Foreign Application Priority Data

Nov. 12, 1993 [FR] France .................. 93 13498

[51] Int. Cl.[6] .................................................. G01N 21/61
[52] U.S. Cl. ........................... 250/343; 250/338.5
[58] Field of Search ........................ 250/343, 353, 250/338.5; 356/437

[56] References Cited

U.S. PATENT DOCUMENTS

| | | | |
|---|---|---|---|
| 4,709,150 | 11/1987 | Burough et al. | 250/338 |
| 4,749,276 | 6/1988 | Bragg et al. | 250/343 |
| 5,026,992 | 6/1991 | Wong | 250/343 |
| 5,053,754 | 10/1991 | Wong | 340/632 |
| 5,060,508 | 10/1991 | Wong | 73/31.02 |
| 5,070,244 | 12/1991 | Simpson | 250/343 |
| 5,103,096 | 4/1992 | Wong | 250/343 |
| 5,163,332 | 11/1992 | Wong | 73/863.23 |
| 5,340,986 | 8/1994 | Wong | 250/338.5 |
| 5,384,640 | 1/1995 | Wong | 250/343 |
| 5,453,620 | 9/1995 | Wadsworth et al. | 250/343 |
| 5,464,983 | 11/1995 | Wang | 250/343 |
| 5,475,222 | 12/1995 | King | 250/343 |

FOREIGN PATENT DOCUMENTS

| | | |
|---|---|---|
| 421100A1 | 8/1990 | European Pat. Off. . |
| 3618690A1 | 6/1986 | Germany . |
| 1398977 | 10/1971 | United Kingdom . |

*Primary Examiner*—Michael J. Tokar
*Assistant Examiner*—Kiet T. Nguyen
*Attorney, Agent, or Firm*—Remy J. VanOphem; Thomas A. Meehan; John VanOphem

[57] ABSTRACT

A device for detecting at least one gas with an absorption band in the infrared range. The device includes a cell containing a gas mixture to be tested, an infrared radiation source, a power supply circuit for the source, an infrared radiation sensor and a signal processing line connected to the output of the sensor. The cell is compact and the radiation source and the radiation sensor are held in direct contact with the gas mixture therein.

21 Claims, 8 Drawing Sheets

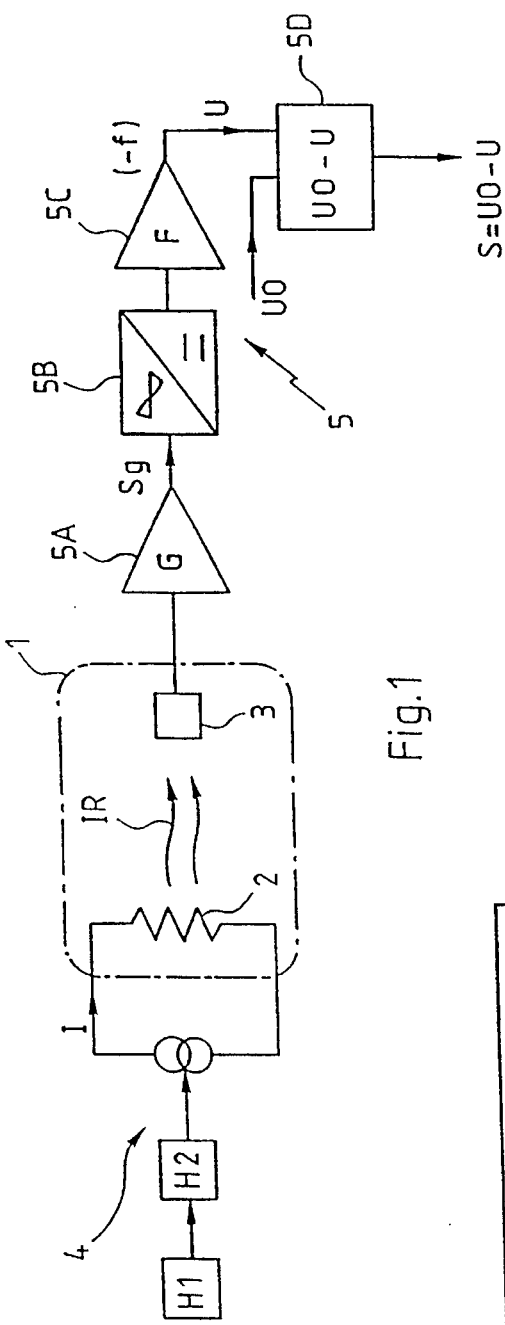
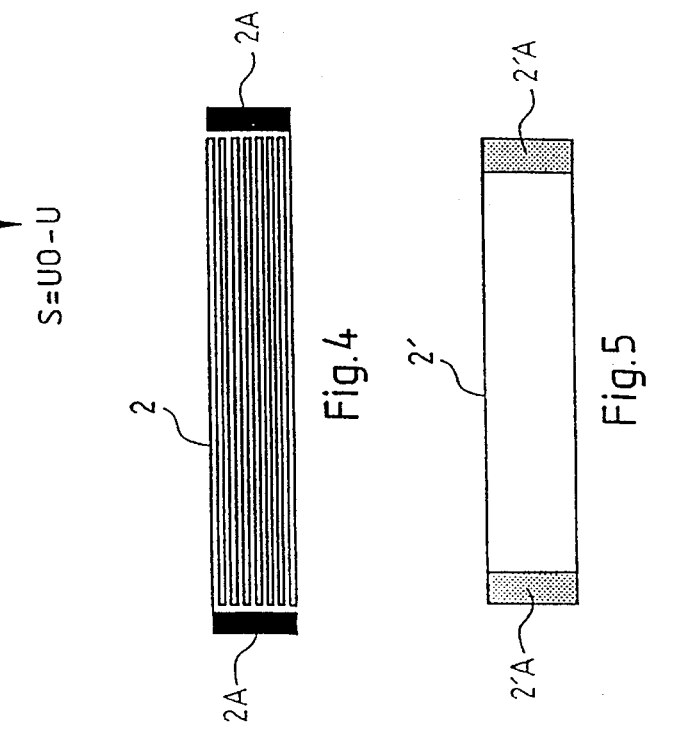
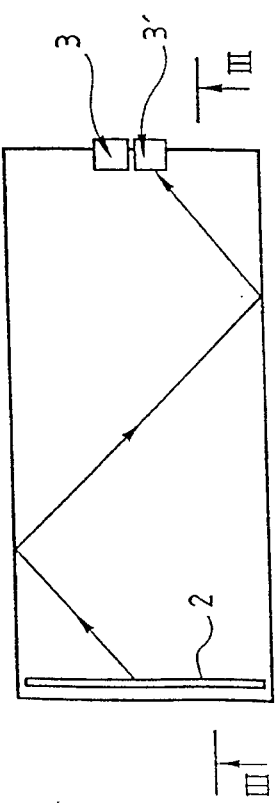
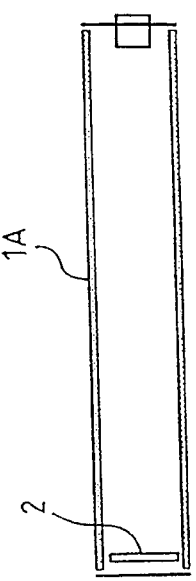
Fig.1
Fig.2
Fig.3
Fig.4
Fig.5

DEVICE FOR DETECTING GAS BY INFRARED ABSORPTION

BACKGROUND OF THE INVENTION

1. FIELD OF THE INVENTION

The invention concerns a device for detecting gases, especially toxic gases, by virtue of their absorption of infrared radiation.

2. DESCRIPTION OF THE PRIOR ART

Very many gases, including hydrocarbons, carbon oxides, water... have absorption bands in the infrared (this does not apply to monoatomic gases or to symmetrical diatomic gases).

For this reason it has already been proposed to use this phenomenon to detect or even to quantify the presence of a gas of this kind in an environment that in principle should not contain it.

For example, this property has been used to detect and to quantify the presence of an undesirable gas such as CO, $CO_2$ or a saturated hydrocarbon (from methane up to butane), or even ammonia or chlorine-containing gases such as trichloroethylene, in an environment based on air that is normally breathable by humans but that has to be monitored (for example in winery cellars, glasshouses, mushroom farms, etc.).

Detectors of this kind are described in U.S. Pat. Nos. 5,026,992; 5,060,508; 5,103,096; 5,053,754; 5,163,332 and 4,709,150 and British Patent No. 1,398,977.

U.S. Pat. No. 5,026,992 proposes a detector in which the infrared radiation is emitted by an IR microsource that can be modulated electrically and embodies a small thin-film or filament resistor made from a material that can heat up and cool down very quickly. This source emits blackbody radiation. The supply of power to it is modulated so that its temperature alternates between two temperatures causing different radiation regimes.

The gas mixture flows transversely to the microsource-detector direction.

The radiation emitted, either before or after passing through the body of gas to be characterized, passes through a filter with two narrow passbands, only one of which contains an absorption band of the undesirable gas to be characterized; the other band is in theory one in which none of the gases likely to be present in the environment to be tested absorbs energy.

A PbSe (or even pyroelectric) photoconductor detector collects the filtered radiation. The signal is then processed to obtain maximal values for each of the power supply regimes of the source. The concentration of the gas to be detected is deduced from the ratio between the aforementioned maximal values.

The extreme temperatures of the source are high (250° C. and 450° C. for methane, for example), which in practice means that the source of radiation cannot be in communication with the gas mixture because of the risk of the source igniting the mixture. In such cases complying with safety standards entails isolating the measurement cell from the source, which imposes a penalty in terms of mass, cost and energy detected.

U.S. Pat. Nos. 5,060,508; 5,163,332; 4,709,150 and British Patent No. 1,398,977 disclose a point source (lamp, for example an incandescent filament in a transparent envelope, possibly at the focus of an ellipsoidal reflector), a detector of a kind specified in varying degrees of detail and, between the source and the detector, a light tube, the walls of which are usually highly reflective, possibly having a zig-zag shape, and running along a wall that is porous to the gases through which some of the gas mixture to be tested penetrates by diffusion. This wall prevents the ingress of any smoke or dust particles, however.

The detector is fitted with selective filters, at wavelengths depending on the gas to be detected.

The use of a point source of light combined with the use of a long light tube or with a porous tube that is presumably not highly reflective would seem to impose a high source temperature, as before, with the risk of ignition in the case of direct contact between the source and the gas to be detected if the latter is explosive. In this regard, it should be noted that the documents under discussion here are primarily concerned with detecting $Co_2$.

It will be realized that the aforementioned structure with a sinuous light tube is complex to manufacture, with probable penalties in terms of cost, weight and overall size.

U.S. Pat. No. 5,103,096 combines the teachings (and the drawbacks) of U.S. Pat. Nos. 5,026,992 and 5,060,508.

SUMMARY OF THE INVENTION

An object of the present invention is to provide a gas detector having the following properties or advantages:

after calibration, the detector is able to detect a wide variety of gases absorbing energy in the infrared, including $CO_2$, $CH_4$, butane and even ammonia, trichloroethylene;

the detector does not contain any hot spots (at a temperature exceeding 100° C., for example) likely to ignite an explosive mixture and does not require the use of a transparent window to isolate the source and/or explosion protection;

the detector's electrical power consumption is low, whence low operating costs and in particular long battery life and therefore portability; note that the less energy the detector requires, the smaller and lighter the batteries needed, and the easier to use and manipulate the detector (it should preferably be possible for the user to carry the detector in a pocket);

the detector is simple in design and light in weight (contributing to ease of manipulation), and also economical, making it financially feasible to use a large number of detectors in a given installation, so enhancing the security of the installation and the safety of persons;

the detector's simple design makes it highly reliable, including in the presence of vibration and even of moderate impact; and the detector can have a fast reaction time (typically less than one minute; the reaction time may depend on the performance of the signal processing electronics chosen, and also on the quantity of the unwanted gas present).

To this end the invention proposes a device for detecting at least one gas having an absorption band in the infrared range, including a cell adapted to contain a gas mixture to be tested, a source of infrared radiation, a power supply circuit for the source including means for generating pulses and by means of which the source of radiation is supplied with power discontinuously, an infrared radiation detector and a signal processor subsystem connected to the output of the radiation detector.

The source of radiation and the radiation detector are contained in the cell, in direct contact with the gas mixture to be tested.

The cell has a compact generally flat closed shape, its length being in a ratio substantially less than 10:1 to its width and its thickness being less than its width, the cell having generally reflective inside walls.

The source of radiation is a thin surface radiation emitter, the surface area of which is significantly greater than the surface area of the radiation detector.

The simple design of a gas detector of this kind is evident (the cell/source/IR detector assembly can be a simple box shape, for example parallelepiped shape). Also, the use of a surface source with a surface area that is in practice several square centimeters enables the use, for a given radiated energy, of a much lower temperature than is required in the aforementioned prior art reference, and therefore provides longer service life. Remember that the radiated energy is proportional to:

$$S(T^4-T_o^4)$$

where

S is the radiating surface area,

T is the temperature of the source,

To is the starting temperature.

For example, a 10 cm² surface source radiates as much energy at 30° C. as a 4 mm² source of 450° C. (for a starting temperature of 20° C.); in this case there is no significant risk of ignition.

The power radiated is typically in the order of a few hundredths of a watt.

The electrical power consumption is all the smaller in that it is discontinuous (energized and non-energized phases alternate). Furthermore, this discontinuous power supply produces a substantially alternating signal at the output of the IR detector which is easy to process.

The flat shape of the detector has the advantage, vis-à-vis a circular cross section, of producing a larger lateral wall area for a given transverse cross section, which facilitates both correct guidance of the radiation by reflection and rapid diffusion of the gases from the exterior (the permeability of the wall in a given area in practice causes local deterioration of its reflecting properties).

Finally, a flat shape enables the use of elongate substantially rectangular thin surface sources, which facilitates connections and produces a more homogeneous emission than thin round surface sources.

The use of thin surface sources has the advantage of reducing overall size, reducing weight and reducing electrical power consumption as compared with solid sources such as described in German Patent No. 3,618,690 in which the emissive surface is merely the end of a heated metal block.

In accordance with preferred features of the invention, some of which may be combined with others:

the cell includes at least one gas-permeable wall;

the gas-permeable wall is parallel to the length and to the width;

the cell has a thickness transversely to its length and to its width significantly less than the length, in a ratio of at least approximately 3:1;

the source has a cross section of at least approximately 1 cm²;

the source has a cross section representing at least 75% of the mean cross section of the cell transversely to the source-detector direction;

the source has a cross section at least equal to the mean cross section of the cell transversely to the source-detector direction;

the source has a cross section significantly greater than the mean cross section of the cell transversely to the source-detector direction;

the source is in the form of two surfaces inclined to each other;

the two surfaces are inclined to the source-detector direction;

the source is in the form of a thin metal film carried by an insulative support layer;

the source includes a copper or aluminum film;

the power supply circuit includes means adapted to independently define the period and the duration of the pulses;

the period and the duration of the pulses are defined so that the output signal of the detector varies in a manner that is at least approximately sinusoidal;

the radiation detector has a narrow passband centered on an absorption band of the gas to be detected;

the radiation detector has a wide passband;

the cell embodies two detectors each having a processor subsystem including a narrowband radiation detector centered on an absorption band of the gas to be detected and a wideband detector;

the detector is a pyroelectric detector; and the thin surface source of radiation is blackened to form a blackbody radiation source.

Objects, features and advantages of the invention will emerge from the following description given by way of non-limiting example with reference to the appended drawings.

BRIEF DESCRIPTION OF THE DRAWINGS

FIG. 1 is block diagram of a gas detector of the invention;

FIG. 2 is a diagrammatic sectional view of the cell of the gas detector;

FIG. 3 is a diagrammatic view of the cell from FIG. 2 in section on the line III—III in FIG. 2;

FIG. 4.is a front view of the source of radiation of the detector from FIGS. 2 and 3;

FIG. 5 is a front view of this source in a different embodiment of the invention;

DETAILED DESCRIPTION OF THE PREFERRED EMBODIMENT

Figure 6A:
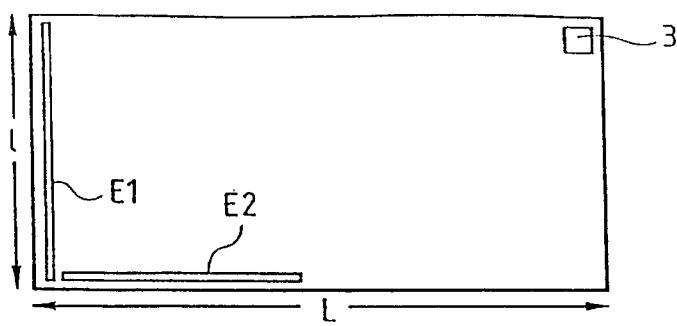
FIG. 6A is a diagrammatic sectional view of a variant of the cell from FIG. 2 with a double source.

As shown in the FIG. 1 block diagram, a gas detector of the invention includes a cell 1, a source 2 of infrared (IR) radiation, an IR radiation detector 3 (possibly fitted with a filter), a power supply circuit 4 connected to the source 2 and a signal processor circuit 5 connected to the IR detector 3. The source and the detector are mounted directly in the cell, in direct contact with the gas to be tested.

The source 2 is a surface source of blackbody radiation and the cross section of which is significantly larger than that of the detector(s). The cross section of the source is typically in the order of several square centimeters (at least 1 cm², in practice between 4 cm² and 20 cm²). In FIGS. 2 and 3 the source has a cross section representing virtually all (more than 75%, up to 90%) of the cross section of the cell.

The source is in the form of a thin electrically conductive resistor carried by a support layer which in practice is made from a plastic material.

In FIG. 4, the source 2 embodies a copper resistor with connection areas 2A printed on a flexible film of the plastic material known as "KAPTON" (a product suitable for etching available from C.I.F. at 11, rue Charles Michels-92220 BAGNEUX-FRANCE can be used). The surface of the resistor and its supporting film are blackened, using ink, for example. The resistor has a resistance of 2 ohms, a cross section of 6 cm² and a copper thickness of 35 μm, for example; during each pulse its power consumption is 3 W at a power supply voltage V=2.5 V.

The electrical power consumption of the source can be reduced, if necessary, by electrolytically thinning the copper layer. However, a radiated power of a few watts (as in the above example) has the advantage of slightly heating the volume of the cell, which prevents the risk of condensation, in particular if the detector is at a fixed location.

It is also feasible to use a laminar heating element such as those sold under the trade name MINCO by AUXITROL at 1, rue d'Anjou-92603 ASNIERES-FRANCE.

In the variant shown in FIG. 5, the source 2' is in the form of a very thin layer or film of aluminum on a plastic material support layer and blackened, for example using ink. The thickness of this layer is typically less than one tenth of a micron; it is a 0.02 μm aluminum film as used in some thermal insulating materials such as survival blankets, for example; its resistance is then typically 10 ohms, resulting in a very low electrical power consumption.

Referring to FIG. 5, the electrical connections 2' A can be made by depositing (e.g. by electrolysis) onto the ends of the aluminum strip a layer of copper, nickel or other metal that can be soldered, to avoid the connection problems associated with the presence of aluminum oxides. Alternatively, the connections can be made by way of small nuts and bolts or by a deposit of silver paste.

The power supply signal supplied by the power supply circuit 4 is discontinuous. To this end a current generator is triggered cyclically by a clock H2 connected to the output of a clock H1 the period T1 of which is greater than the period T2 of the clock H2. The benefit of combining two clocks is obtaining a stream of pulses at a frequency set by H1 with a duration set by the period of H2; thus the frequency and the length of the pulses can be defined separately. T2 is in the order of T1/2, for example, with the result that the pulse length is in the order of ¼ the pulse period. In the FIG. 7 example a single clock is sufficient, the length of the pulses being half the period and the signal Sg being approximately sinusoidal.

The frequencies of H1 and H2 are in principle adjusted to minimize electrical power consumption (by adjustment of the active power supply time) and to render the output signal of the detector 3 as close to sinusoidal as possible (see below).

The cell 1 has a compact shape, preferably a generally parallelepiped shape with a length L greater than the width 1 which in turn is greater than the thickness h.

In principle (although this is not mandatory), the source 2 and the detector 3 are offset parallel to the lengthwise direction; as mentioned above, the source typically has an area at least in the same order as the cross section (h×l) f the cell.

The gas to be measured preferably penetrates into the cell via a wall 1A of the cell. This wall is advantageously permeable to the gases while preventing any ingress of dust. Of course, the walls must prevent any unwanted ingress of radiation in the operating passband of the detector 3.

The preamble wall 1A can in practice be a plastic material (e.g. PTFE) membrane or a rigid material with open pores (such as a sintered metal, bronze or stainless steel, for example).

Alternatively, the gas can penetrate through very small holes (diameter typically between 10 μm and 500 μm).

Evidently, the larger the area of the diffusion wall 1A and the shorter the dimension of the cell perpendicular to the wall 1A, the faster the composition of the gas mixture in the cell homogenizes, even at low concentrations. This is why the diffusion wall 1A is preferably the wall parallel to the length and to the width of the cell and the thickness h is as small as possible (typically in the order of one centimeter). This explains why a cell according to the invention is preferably flat.

Penetration can also take place through other walls of the cell, of course.

Two cell geometries have been tested:
cell C1 (internal volume approximately 64 cm³)

L=8.5 cm (external length: 10 cm)

l=5 cm (external width: 6.7 cm)

h=1.5 cm (external height: 1.8 cm)

cell C2 (internal volume approximately 310 cm³)

L=18 cm (external length: 20 cm)

l=7.9 cm (external width: 10 cm)

h=2.2 cm (external height: 2.7 cm)

source-IR detector distance: 17.5 cm

Cell C1 included either a copper source (FIG. 4) 5.5 cm long (exploiting the fact that this source was a flexible circuit that could be curved with the concave side towards the detector) or an aluminum source 4.5 cm long.

Cell C2 was used with copper emitters (5.5 cm long as previously stated).

Although one of the back walls of the cell can mostly be occupied by a source, as just stated with regard to copper sources, the source can equally well extend onto the lateral walls.

The source can even extend a significant distance over one of the lateral walls of the cell.

Figure 6B:
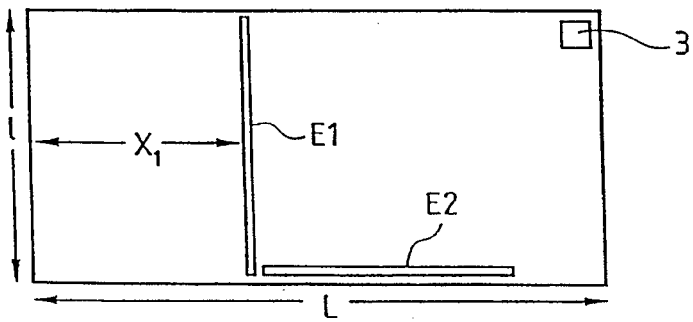
FIG. 6B shows a second variant of the cell also with a double source.
Figure 6C:
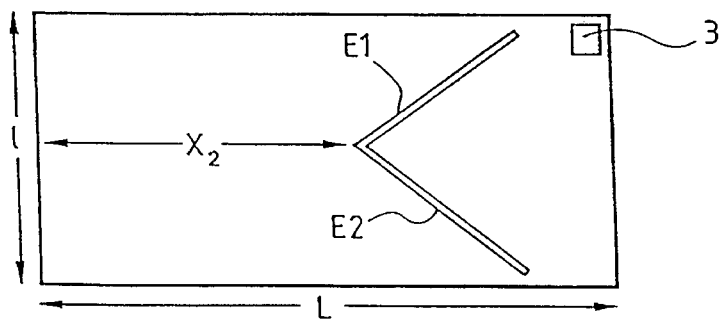
FIG. 6C shows a third variant of the cell, also with a double source.

Accordingly, FIGS. 6A through 6C show configurations with two substantially identical copper emitters E1 and E2 mounted in series and constituting a double source.

In FIG. 6A one emitter E1 is at the left-hand back of the cell and the other emitter E2 extends along one wall.

In FIG. 6B the combination E1+E2 is moved a distance $x_1$ towards the back wall.

In FIG. 6C the combination E1+E2 is moved a distance $x_2$ towards the right-hand back wall, each of the emitters being inclined towards the other vis-à-vis the emitter-detector direction.

In each case the detector 3 is in one corner of the cell.

Various tests have been conducted for these various configurations (with $x_1$=4.5 cm and $x_2$=9.5 cm). The results of these tests are commented on with reference to FIG. 11.

The internal surface of the cell is designed to reflect the incident radiation; the reflecting surface is preferably the surface of the material from which the walls are made. This is metal, for example, such as aluminum anodized to prevent slow oxidation and therefore drift in the signal due to the changing state of the walls; in this case the detector can be used in oxidizing atmospheres.

The IR radiation detector 3 is a pyroelectric detector, i.e. a detector supplying a signal proportional to the quantity of heat that it receives. In principle it includes a black surface on which the radiation to be detected impinges. It is, for example, an infrared pyroelectric detector of the IRA type marketed by MURATA MFG CO. LTD.

Infrared pyroelectric detectors are usually intruder detectors, designed to detect infrared radiation given off by the body of an intruder. The invention gives them a different function in that they detect a reduction in the energy received from a source.

The IR energy received at the black surface of the detector induces an output signal which varies in sympathy with that energy.

One benefit of a discontinuous power supply to the source is that the signal can be caused to vary sinusoidally (see above).

The output signal is amplified by a selective amplifier 5A of gain G centered on the pulse frequency, and then rectified by a rectifier 5B; it is then filtered by a filter 5C to eliminate frequency components equal to the pulse frequency. This produces a signal U which is subtracted (5D) from a reference signal $U_o$ (equal to U in the absence of any absorption in the band of the detector 3). The different signal S is representative of the concentration of the gas in question.

The voltage $U_o$ and the gain G can be varied to compensate for atmospheric effects (pressure and temperature), using temperature and pressure sensors if necessary.

FIG. 2 shows two detectors 3 and 3' which can have different characteristics.

Specifically, they can be:

a narrowband detector centered on the absorption band of the gas to be measured (4.3 μm for $CO_2$ or 3.3 μm for $CH_4$, for example), and a wideband detector (1 μm–20 μm, for example) which can detect $H_2O$ spectral lines in the presence of moisture, and even other spectral lines of the gas in question, for example; to prevent the sensitive part of the detector from receiving too much energy, it can be preceded by a filter of greater or lesser opacity (in practice this can be a mica filter or a more absorbent filter known as a total filter).

The detectors can be duplicated, with two similar detector elements, the difference between the outputs of which is fed to the input of the processing subsystem. Sometimes a filter is placed in front of one of the detector elements, in order to increase the signal fed to the processing subsystem. A total filter is a filter which stops all wavelengths.

A narrowband detector $B_o$ is usually a detector whose passband is a fraction of a micron (0.1 μm to 0.9 μm) whereas a wideband detector has a passband exceeding a few microns.

If two detectors are used simultaneously they can be processed simultaneously by one processor subsystem (especially if they are identical) or separately by parallel subsystems (in particular if more than one gas must be detected at the same time, using different detectors). The use of two separate detectors has advantages including the possibility of determining whether there is one or more than one unwanted gas present, and the nature of the gas(es) (see below).

Figure 7:
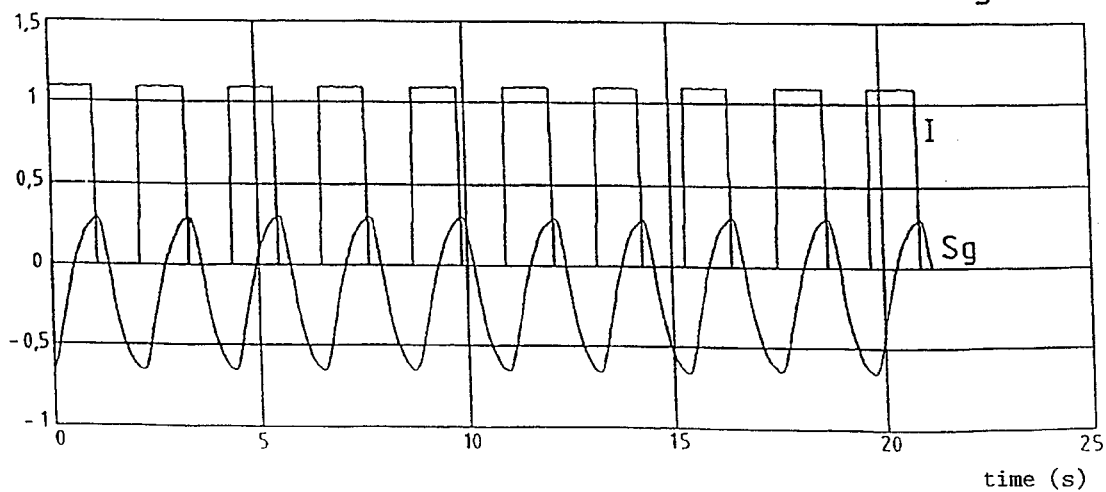
FIG. 7 is a graph showing the typical trend of the power supply signal and the detected signal as a function of time.

Referring to FIG. 7, the signal I varies between 0 and 1.1 A; the amplitude of Sg is expressed in arbitrary units dependent on the gain G, with maxima which usually coincide with the end of the power supply pulses.

FIGS. 8A through 10 show the variation with time of the signal S obtained for various gases in various configurations.

Figure 8A:
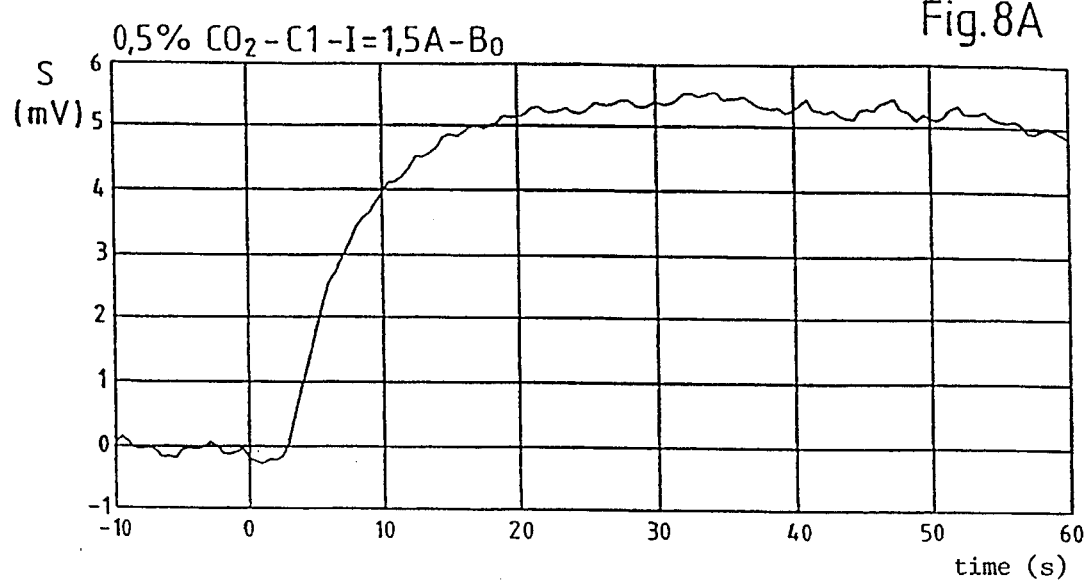
FIG. 8A is a graph showing the variation with time of the output signal for 0.5% $CO_2$ in a first cell, with a copper emitter, a supply current of 1.5 A and a narrowband detector centered on 4.4 μm.
Figure 8B:
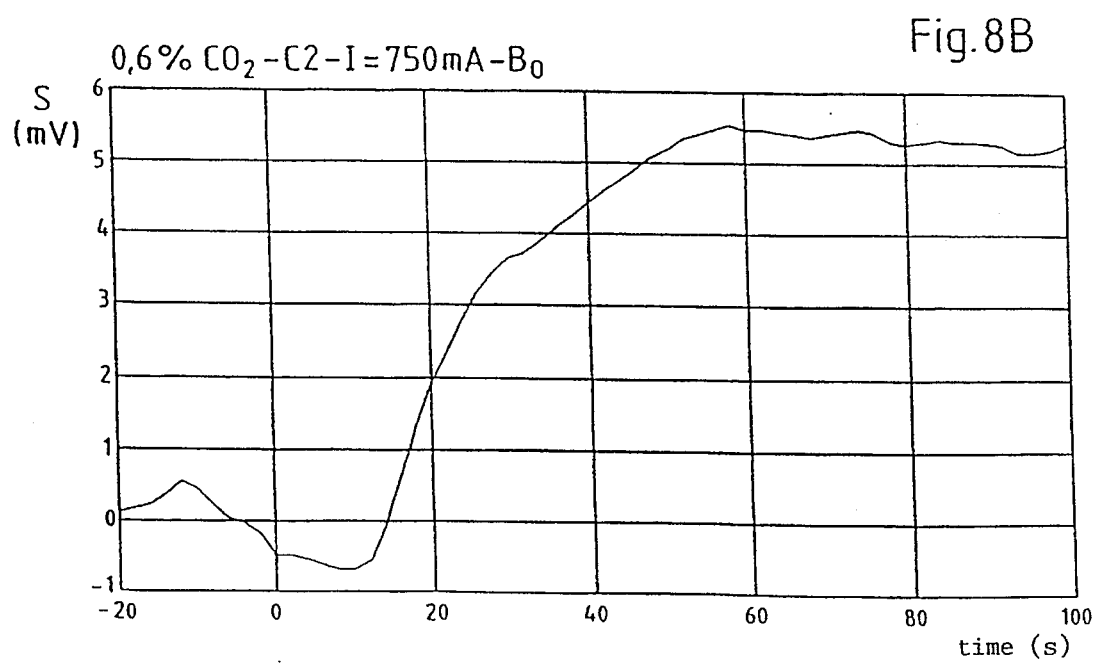
FIG. 8B is a similar diagram for 0.6% $CO_2$ in a second and larger cell with two copper emitters in the FIG. 6A configuration, a supply current of 0.75 A and the same detector.

FIGS. 8A and 8B correspond to similar concentrations (respectively 0.5% and 0.6%) of $CO_2$ in air in the small cell C1 and then in the large cell C2.

Figure 9A:
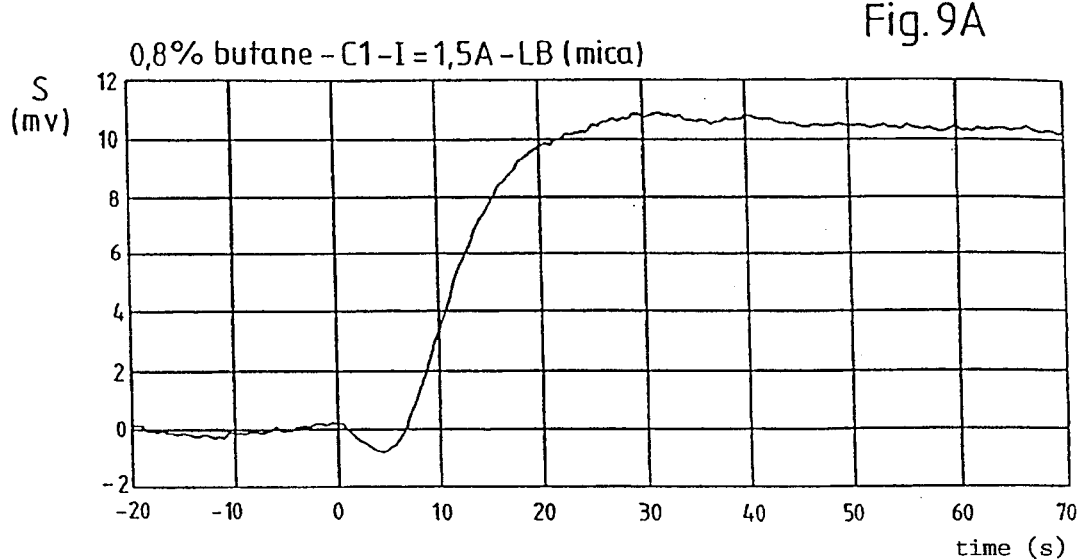
FIG. 9A is a similar graph for 0.8% butane in the same configuration as FIG. 8A but with a 1 μm–20 μm detector fitted with a mica filter.
Figure 9B:
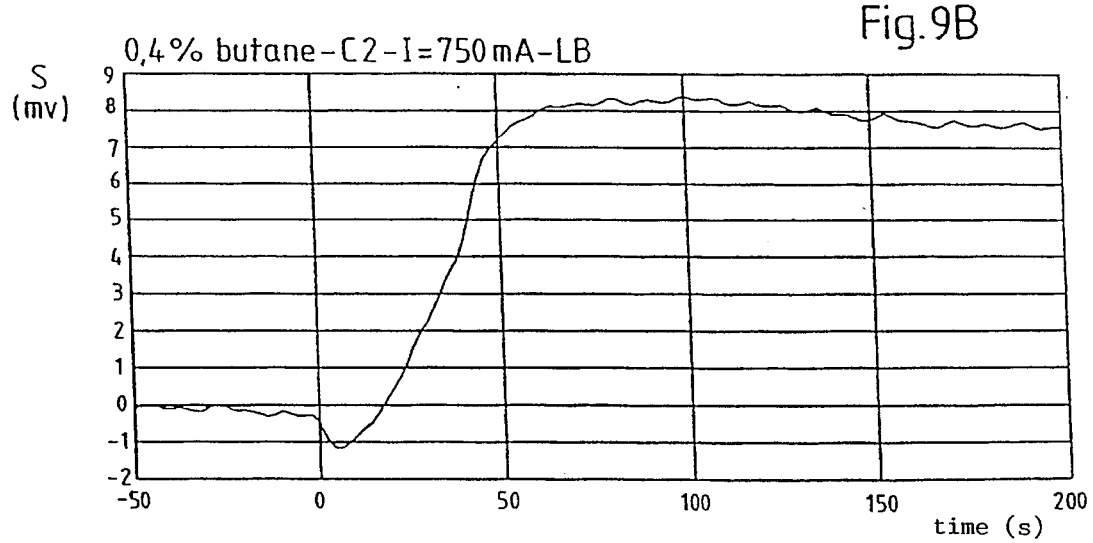
FIG. 9B is a similar graph for 0.4% butane in the same configuration as FIG. 8B but with a 1 μm–20 μm detector.

Likewise, FIGS. 9A and 9B correspond to 0.8% and 0.4%, respectively, of commercial butane in air in C1 and then in C2.

Figure 10:
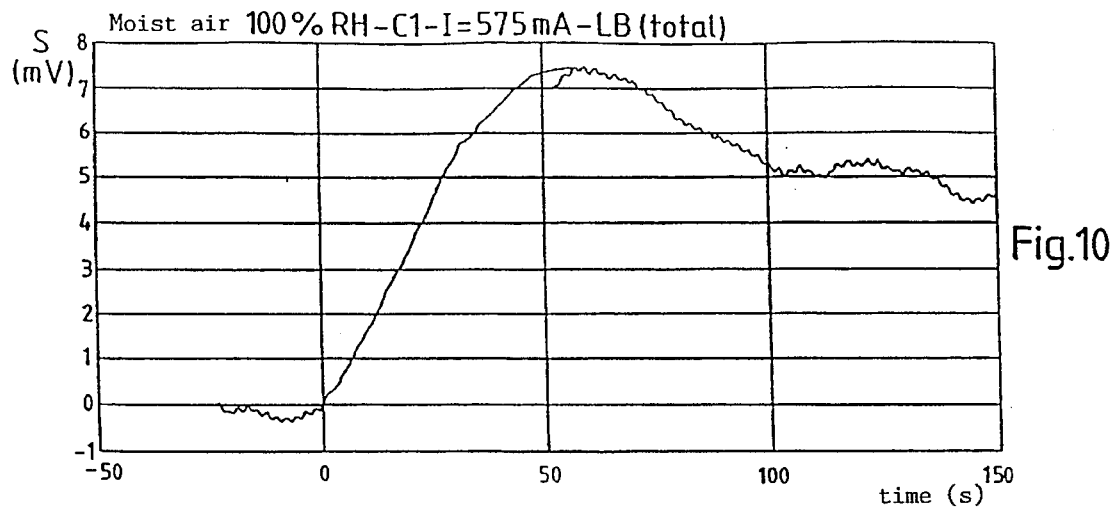
FIG. 10 is a graph similar to those of FIGS. 8A and 9A for moist air at 100% RH with a supply current of 0.575 A, a 1 μm–20 μm detector and a total filter.

Finally, FIG. 10 corresponds to water vapor (moist air at 100% RH) in the small cell C1.

The cell C1 was fitted with a copper emitter with a power supply current I of 1.5 A (FIGS. 8A and 9A) or 575 mA (FIG. 10). The cell C2 was fitted with two copper emitters in the FIG. 6A configuration with a power supply current I of 750 mA.

The detector was either a narrow band ($B_o$) detector centered on 4.4 μm (FIGS. 8A and 8B) or a wideband (LB) detector with a mica filter (FIG. 9A), no filter (FIG. 9B) or a total filter (FIG. 10).

As might be expected, no variation was found with detector $B_o$ in the case of moist air.

Gas was injected at time t=0 using a syringe. The resulting disturbance corresponded to a very short-term reduction in the signal level.

The reduction in the signal level after the maximum was attributed to leaks to the exterior (the ordinary surrounding air).

These artifacts were particularly large in the case of moist air and it is thought that condensation was present. It would seem that a time-delay of 100s should be observed before monitoring the wanted signal.

Cell C1 was fitted with a dedicated signal commercially available processing circuit for gas detector applications (Analog Devices AD737). Cell C2 was equipped with standard operational amplifiers. This explains why the response time is 30s for FIGS. 8A and 9A and 60 s for FIGS. 8B and 9B.

Figure 11:
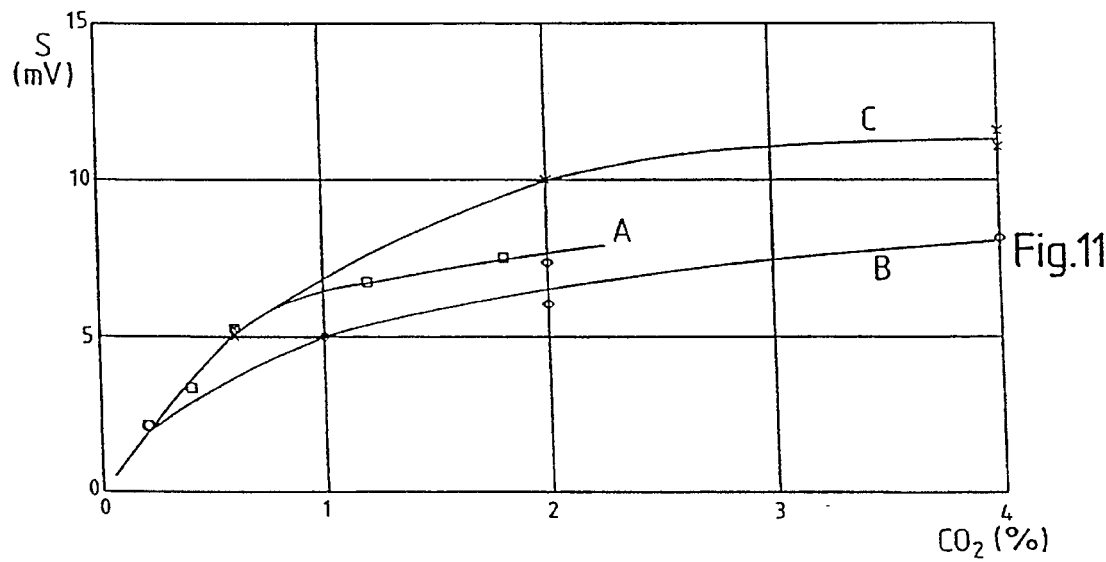
FIG. 11 is a graph showing the signal obtained as a function of the $CO_2$ concentration in the second cell with a 4.4 μm detector for the three source configurations of FIG. 6A (squares), FIG. 6B (lozenges) and FIG. 6C (crosses)

FIG. 11 shows the effect of the mounting of the emitters in the cell C2 for various concentrations of $CO_2$ (using a $B_o$ detector), curve A corresponding to the FIG. 6A arrangement, curve B to FIG. 6B and curve C to FIG. 6C. Note that the influence is relatively slight although the sensitivity is better for curve C with the emitters closer to the detector (the width and the length of the volume between the emitters and the detector were approximately the same).

FIGS. 12A through 14C show the variation in the signal S for various gases, in various concentrations and with various cell, emitter (Cu or Al) and detector (with or without filter) configurations.

Figure 12A:
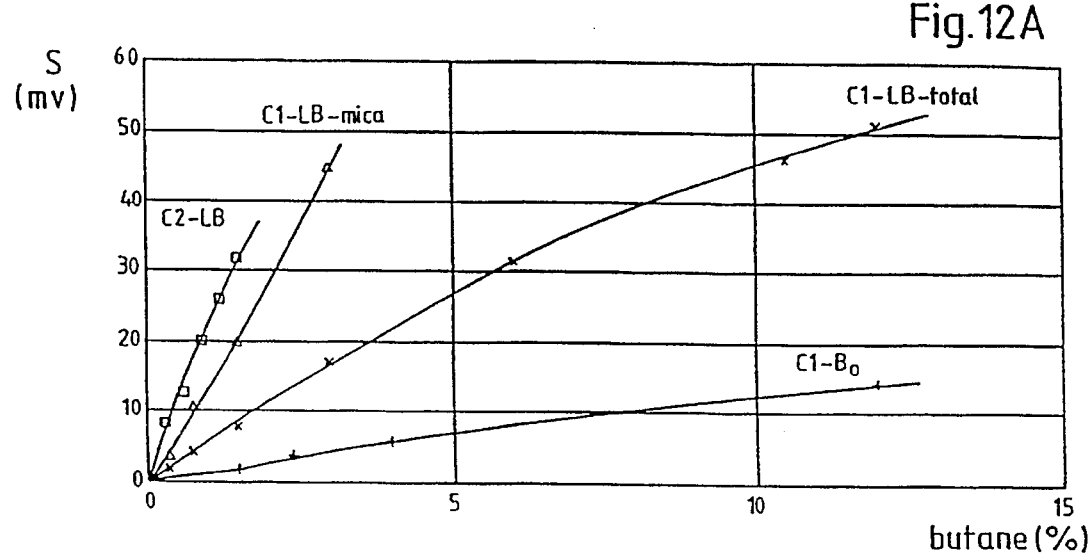
FIG. 12A is a graph showing the response for different concentrations of butane as a function of the cell and the IR detector used.
Figure 12B:
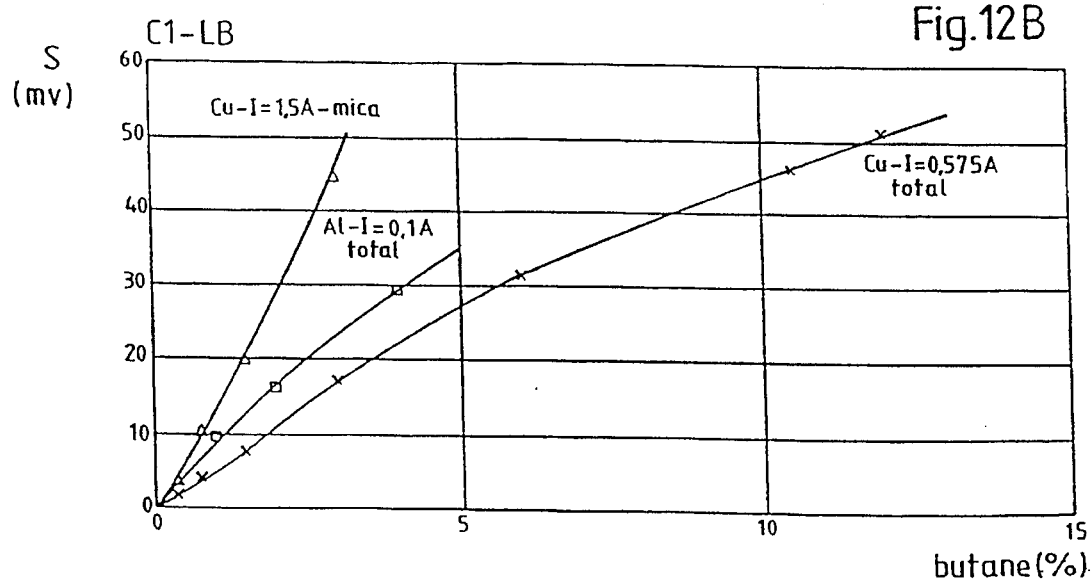
FIG. 12B is a similar graph, also for butane, in the first cell and with the wideband 1 μm–20 μm detector, for various emitters.
Figure 14:
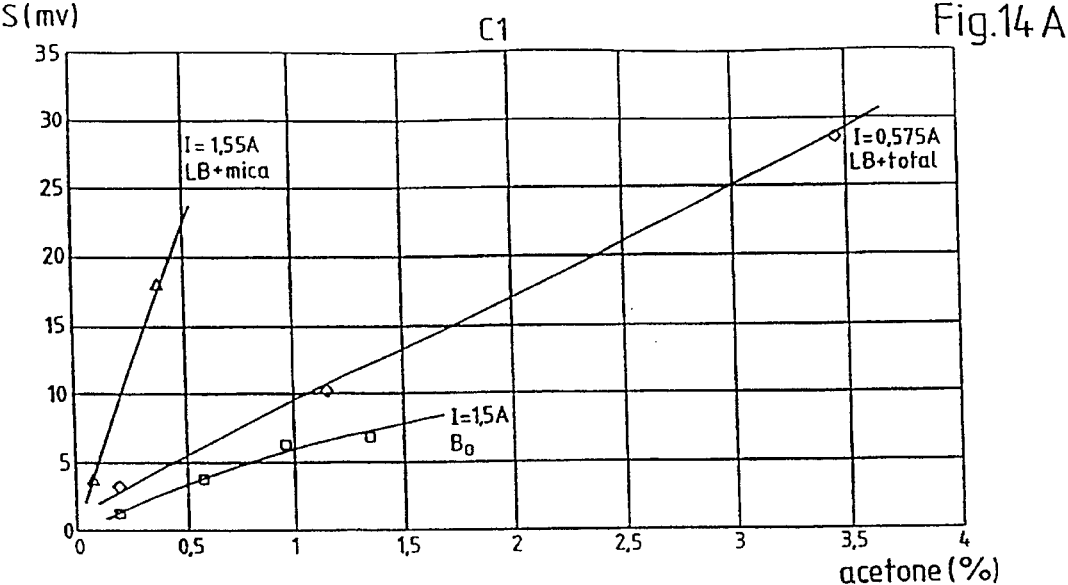
FIG. 14A is a similar graph for acetone in the first cell as a function of the detector used.
FIG. 14B is a similar graph for ammonia.
FIG. 14C is a similar graph for trichloroethylene.
Figure 14:
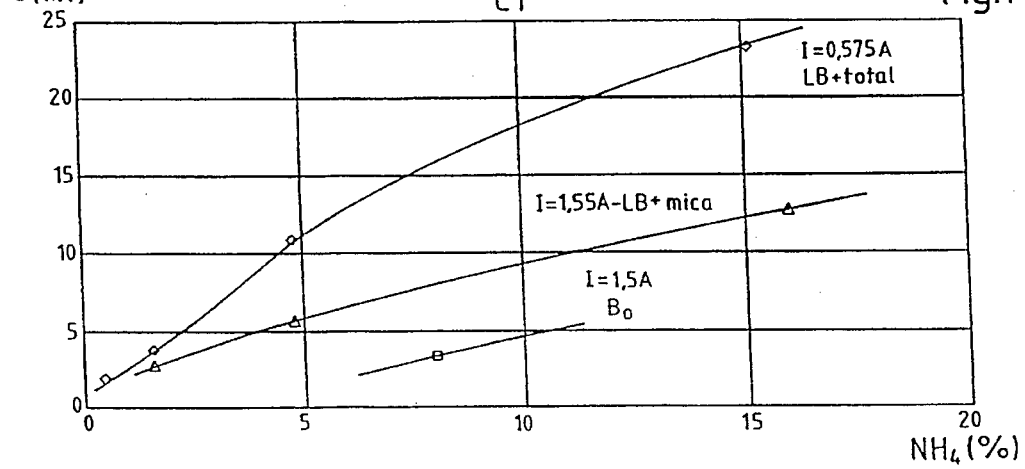
Figure 14:
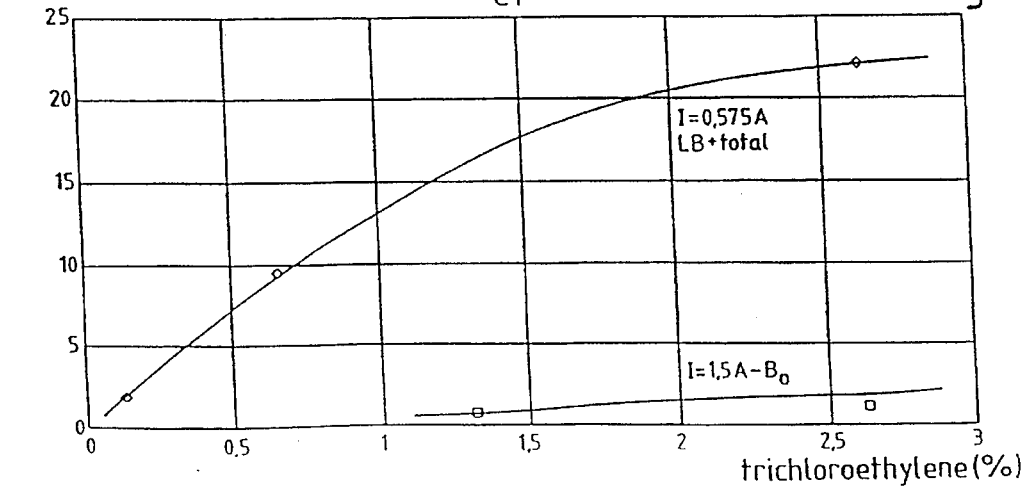

FIGS. 12A and 12B correspond to commercial butane.

Note that the sensitivity increases on changing from a narrowband $B_o$ detector to a wideband LB detector with a total filter, then a mica filter, then no filter. With the same filter, the sensitivity increases on changing from a Cu emitter to an Al emitter, even if the current is reduced by a coefficient in the order of six.

Figure 13:
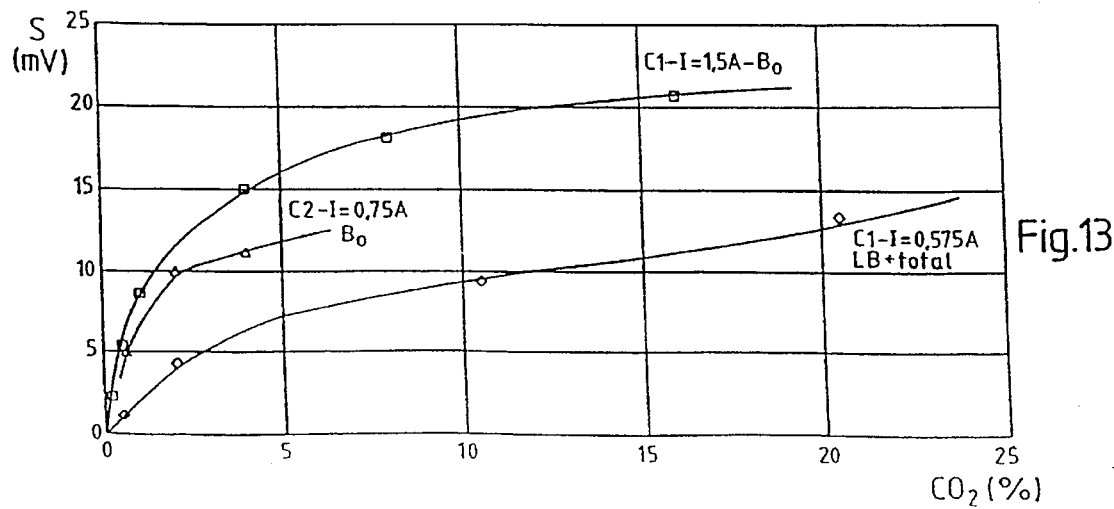
FIG. 13 is a similar graph for $CO_2$ as a function of the cell and the detector used.

FIG. 13 corresponds to $CO_2$.

Sensitivity is better for a $B_o$ detector than for an LB detector (with a total filter and, it is true, a lower value of I).

FIGS. 14A through 14C correspond to acetone in air, ammonia in air and trichloroethylene in air.

The absorption bands of the gases concerned show different sensitivities in the same order of magnitude (remember that $B_o$ is not necessarily centered at 4.4 μm).

Figure 15:
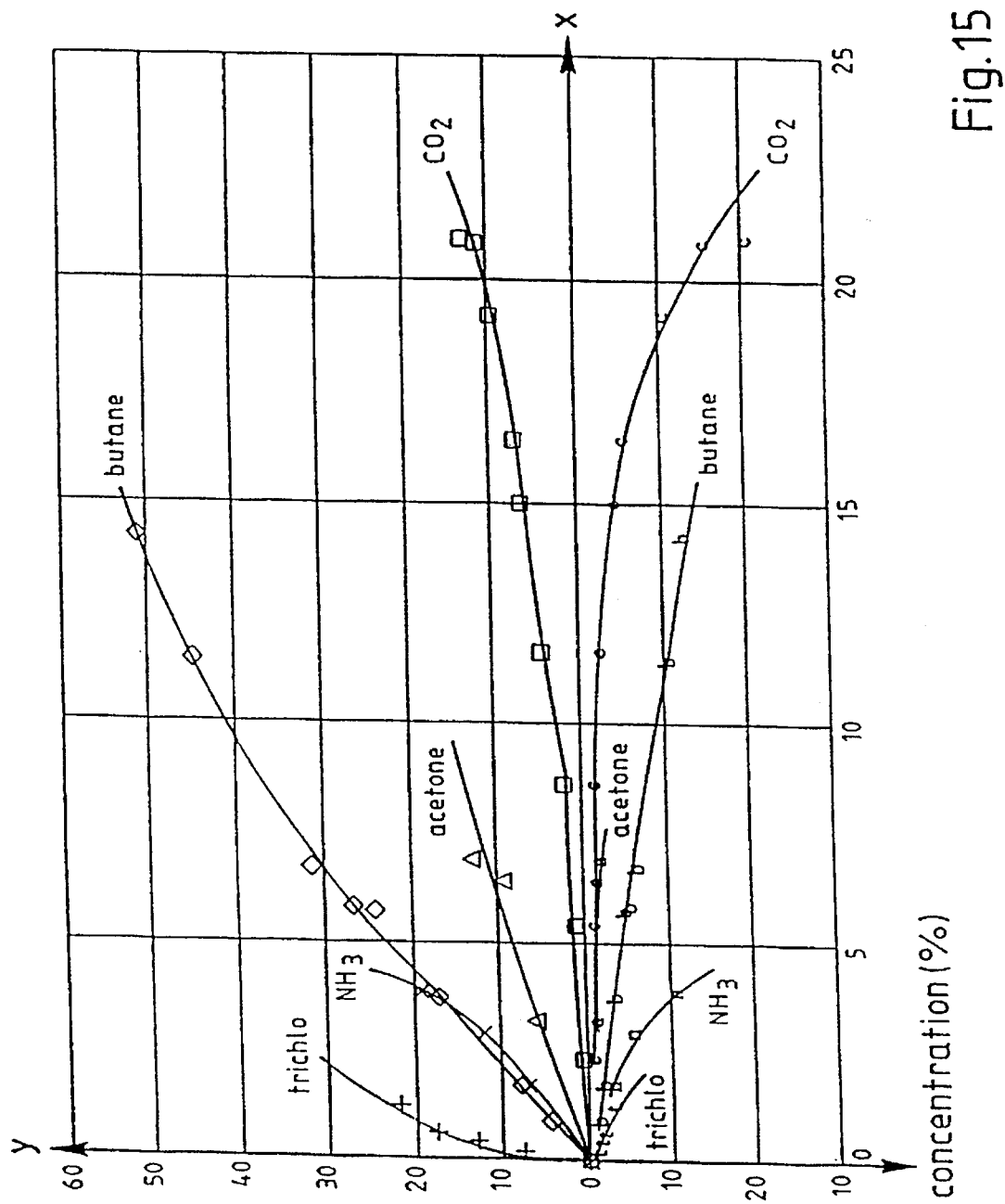
FIG. 15 is a summary graph correlating, for various gases in various concentrations, the signals obtained with each of the two detectors (narrowband and wideband) used, and giving the concentration of the gas.

FIG. 15 summarizes various results, showing the correlation between the value of the signal obtained with a $B_o$ detector and, at the top, the value of the signal obtained (for the same mixture) with an LB detector and a total filter and, at the bottom, the percentage concentration of the gas concerned.

A figure of this kind can be used in the following way when, as in FIG. 2, the gas detector includes a $B_o$ detector and an LB detector (plus total filter) with separate processor subsystems producing output signals x (for $B_o$) and y (for LB).

The point at coordinates (x, y) is marked on the FIG. 15 diagram. If it aligns with points already established for a particular gas, then it is this gas which has been detected. All that is required is then to look up the sensitivity curve for this gas for one or other of the detectors in order to determine the concentration.

In the case of a two-component gas mixture, for example $CO_2$ and water vapor, it is possible to measure the concentration of each component.

Considering the $CO_2$ sensitivities ($a_1$ and $a_2$ constant for concentrations of $CO_2$ in air less than 2%), and assuming that the sensitivity to water vapor ($b_2$) is also constant: the signal from the $B_o$ detector is $x=a_1 x_1$, and the signal from the LB detector is $y=a_2 x_1 + B_2 x_2$, where $x_1$ is the concentration of $CO_2$ and $x_2$ is the concentration of water vapor or the relative humidity RH, whence $x_1$ and $x_2$ can be determined as follows:

$x_1 = x/a_1$ $x_2 = (a_1 y - a_2 x)/a_1 b_2$

It goes without saying that the above description has been given by way of non-limiting example only and that many variants can be proposed by the person skilled in the art without departing from the scope of the invention.

In particular, the parallelepiped shape of the cell can be replaced with other compact and preferably flat shapes; in particular, the width of the cell can vary along its length (yielding a trapezoidal shape, for example, with the longer base occupied by the surface source (or emitter); as indicated implicitly in FIG. 5C, the width and the length can be interchanged (i.e. the emitter-detector distance can either be less than or greater than the mean cross section of the cell between the emitter and the detector). In this context a compact shape is a shape whose two greater dimensions, called the length and the width, are in a small ratio (less than one order of magnitude (i.e. less than 10), preferably less than 2, or even 3), the third dimension, called the thickness or height, possibly being much smaller than the length (in a ratio of 3:1, or even 5:1 or more).

The surface of the internal walls can be directionally reflective or even (and more simply) matt frosted (to reflect light impinging on it diffusely).

When more than one detectors are used, their passbands can be contiguous or noncontiguous, as appropriate.

Instead of a pyroelectric detector, the detector can be one based on PbSe, PbS, HzCdTe, InSb or InAs (these components are manufactured by the Japanese company HAMAMATSU which has an office in France at PARAY VIEILLE POSTE, 91781 WISSOUS).

An alternative to signal processing by rectifying a sinusoidal signal is to sample and store the peak signal or the signal averaged over a short time interval up to the duration of the positive or negative signal produced by the detector, following a single pulse. This enables adjustment of H1 and H2 to optimize the mean electrical power consumption of the emitter, by reducing the pulse frequency and the pulse duration (for example a 10 ms (0.01 s) pulse every 6 seconds).

Another way to introduce the gas into the tank is to use a pumping system.

What is claimed is:

1. A device for detecting at a given gas having an absorption band in the infrared range comprising:

a compact closed chamber for containing a gas sample to be detected for the presence of the given gas, said compact closed chamber having a predetermined width, a length less than ten times that of said predetermined width, and a thickness less than said predetermined width, said compact closed chamber having reflective interior walls;

a detector member located within said compact closed chamber, said detector member having a predetermined surface area, said detector member directly contacting said gas sample;

an infrared radiation source located within said compact closed chamber, said infrared radiation source having a thin surface radiation emitter in direct contact with said gas sample, said thin surface radiation emitter having a surface area greater than said predetermined surface area of said detector member;

means for supplying discontinuous power, said supply means connected to said infrared radiation source; and a signal processor subsystem connected to said detector member whereby a signal generated by said infrared radiation source is communicated to said detector member through said gas sample such that said signal supplied by said detector member is processed by said signal processor subsystem to determine said presence of said gas in said compact closed chamber.

2. The device according to claim 1 wherein said compact closed chamber includes at least one gas-permeable wall.

3. The device according to claim 2 wherein said at least one gas-permeable wall is parallel to said length and said predetermined width of said compact closed chamber.

4. The device according to claim 1 wherein said thickness of said compact closed chamber is transverse to said length and to said predetermined width, said predetermined width being less than said length in a ratio of at least approximately 3:1.

5. The device according to claim 1 wherein said infrared radiation source has a cross section of at least approximately 1 cm$^2$.

6. The device according to claim 1 wherein said infrared radiation source has a cross section representing at least 75% of a mean cross section of said compact closed chamber transverse to said length of said compact closed chamber.

7. The device according to claim 6 wherein said infrared radiation source has a cross section at least equal to said mean cross section of said compact closed chamber.

8. The device according to claim 7 wherein said infrared radiation source has a cross section greater than said mean cross section of said compact closed chamber.

9. The device according to claim 7 wherein said infrared radiation source further comprises two surfaces inclined towards each other.

10. The device according to claim 9 wherein said two surfaces are inclined in a direction of said length of said compact closed chamber.

11. The device according to claim 1 wherein said infrared radiation source comprises an insulative support layer and a thin metal film carried by said insulative support layer.

12. The device according to claim 11 wherein said thin metal film comprises copper.

13. The device according to claim 11 wherein said thin metal film comprises aluminum.

14. The device according to claim 1 wherein said means for supplying discontinuous power further comprises means to independently define a period and duration of pulses.

15. The device according to claim 14 wherein said period and duration of pulses are defined so that an output signal of said detector member is approximately sinusoidal.

16. The device according to claim 1 wherein said detector further comprises a narrow passband centered on an absorption band of a gas to be detected from said sample of gas.

17. The device according to claim 1 wherein said detector further comprises a wide passband.

18. The device according to claim 1 wherein said detector member is a pyroelectric detector.

19. The device according to claim 1 wherein said infrared radiation source is blackened to form a blackbody radiation source.

20. The device according to claim 1 wherein said detector member comprises:

a narrowband detector member having a range centered on an absorption band of said gas to be detected from said gas sample; and a wideband detector member located within said compact closed chamber.

21. The device according to claim 20 wherein said signal processor subsystem comprises:

a first processor subsystem connected to said narrowband detector member for processing a signal supplied by narrowband detector member; and a second processor subsystem connected to said wideband detector member for processing a signal supplied by said wideband detector member.

* * * * *

UNITED STATES PATENT AND TRADEMARK OFFICE
CERTIFICATE OF CORRECTION

PATENT NO. : 5,608,219
DATED : March 4, 1997
INVENTOR(S) : Cécile Aucremanne

It is certified that error appears in the above-identified patent and that said Letters Patent is hereby corrected as shown below:

Column 4, line 43, delete "4.is" and insert ---- 4 is ---- .

Column 6, line 41, delete "f" and insert ---- of ---- .

Column 10, line 42, delete "at".

Column 12, line 31, after "by" insert ---- said ---- .

Signed and Sealed this

Fifth Day of May, 1998

Attest:

BRUCE LEHMAN

Attesting Officer

Commissioner of Patents and Trademarks